(12) United States Patent
Koehler

(10) Patent No.: US 7,393,555 B2
(45) Date of Patent: *Jul. 1, 2008

(54) DICOPPER(I) OXALATE COMPLEXES AS PRECURSOR FOR METALLIC COPPER DEPOSITION

(75) Inventor: Katrin Koehler, Goettingen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 191 days.

This patent is subject to a terminal disclaimer.

(21) Appl. No.: 10/554,736

(22) PCT Filed: Mar. 29, 2004

(86) PCT No.: PCT/EP2004/003313

§ 371 (c)(1),
(2), (4) Date: Oct. 28, 2005

(87) PCT Pub. No.: WO2004/096816

PCT Pub. Date: Nov. 11, 2004

(65) Prior Publication Data

US 2007/0037003 A1   Feb. 15, 2007

(30) Foreign Application Priority Data

Apr. 29, 2003  (DE)  ................. 103 19 454

(51) Int. Cl.
*B05D 5/12*  (2006.01)
*B32B 15/00*  (2006.01)
*C07F 1/00*  (2006.01)

(52) U.S. Cl. .................. 427/124; 428/615; 556/113
(58) Field of Classification Search .............. None
See application file for complete search history.

(56) References Cited

U.S. PATENT DOCUMENTS

| | | | |
|---|---|---|---|
| 4,387,055 A | 6/1983 | Doyle | |
| 5,220,044 A | 6/1993 | Baum et al. | |
| 5,441,766 A * | 8/1995 | Choi et al. | 427/250 |
| 6,130,345 A | 10/2000 | Doppelt | |
| 7,169,947 B2 * | 1/2007 | Koehler et al. | 556/113 |

FOREIGN PATENT DOCUMENTS

| | | |
|---|---|---|
| DE | 41 24 686 | 1/1992 |
| EP | 0 297 348 | 1/1989 |
| EP | 0 468 396 | 1/1992 |
| WO | 00 08225 | 2/2000 |
| WO | 00 17278 | 3/2000 |
| WO | 00 63461 | 10/2000 |
| WO | 00 71550 | 11/2000 |
| WO | 2004 000850 | 12/2003 |

OTHER PUBLICATIONS

Koehler et al. "Dicopper(I) Oxalate Complexes Stabilized by Lewis Bases: Potential Precursors for Copper Deposition", Organometallics, vol. 22, pp. 4426-4432 2003.
Diez et al. "Preparation of new mono and polynuclear bis(triphenylphosphine) copper(I) derivatives containing mono and bidentate N-heterocycles, 8-hydroxyquinoline and oxalate ligands", CAPLUS, English abstract only 1988.
Chen et al. "2-Methyl-1-hexen-3-yne Lewis Base Stabilized beta-Diketonate Copper(I) Complexes: X-ray Structures, Theoretical Study, and Low-Temperature Chemical Vapor Deposition of Copper Metal", Chem. Mater., vol. 13, pp. 3993-4004 2001.
Chen et al. "Formation Study and X-ray Structures of Dinuclear beta-Diketonate Copper(I) Complexes with Conjugated Ene-Yne Lewis Base. Implications for the Use of (hfac)Cu(MHY) as a Precursor for Copper CVD", Inorg. Chem., vol. 40, pp. 6167-6171 2001.
Baum et al. "A Novel Copper Complex and CVD Precursor: (η2-2-Butyne)copper(I) Hexafluoroacetylacetonate", Chem. Mater., vol. 4, pp. 365-369 1992.
Rozenberg et al. "Synthesis and Spectroscopic Studies of Novel beta-Diketonate Copper(I) Compounds and Solid State Structure of Tetravinylsilane Tetrakis Copper(I) 1,1,1,5,5,5-Hexafluoroacetylacetonate (TVST[Cu]hfac)", Organometallics, vol. 20, pp. 4001-4005 2001.
Lang et al. "Monomere (Acetylacetonato)kupfer(I)-Komplexe von Alkinen und 1,4-Diinen", Chem. Ber., vol. 128, pp. 525-529, with English abstract 1995.
Doppelt et al. "Chemical Vapor Deposition of Copper for IC Metallization: Precursor Chemistry and Molecular Structure", MRS Bulletin, pp. 41-49 1994.
Kumar et al. "Copper(I) Precursors for Chemical Vapor Deposition of Copper Metal", Chem. Mater., vol. 4, pp. 577-582 1992.

* cited by examiner

*Primary Examiner*—Yvonne Eyler
*Assistant Examiner*—MLouisa Lao
(74) *Attorney, Agent, or Firm*—Oblon, Spivak, McClelland, Maier & Neustadt, P.C.

(57) ABSTRACT

The invention relates to dicopper(I) oxalate complexes stabilized by neutral Lewis bases, such as alkenes or alkynes, and to the use of dicopper(I) oxalate complexes as precursors for the deposition of metallic copper, in which the neutral Lewis bases used are alkynes, alkenes, triarylphosphines, CO or isonitriles.

23 Claims, 2 Drawing Sheets

DICOPPER(I) OXALATE COMPLEXES AS PRECURSOR FOR METALLIC COPPER DEPOSITION

The invention relates to dicopper(I) oxalate complexes stabilised by neutral Lewis bases, such as alkenes or alkynes, and to the use of dicopper(I) oxalate complexes as precursor for the deposition of metallic copper, in which the neutral Lewis bases used are alkynes, alkenes, triarylphosphines, CO or isonitriles.

PRIOR ART AND OBJECTS OF THE INVENTION

Many organocopper precursors are now known for the deposition of thin copper films on substrates. Highly promising substances have proven to be copper compounds in oxidation state +1 which contain a β-diketonate ligand and a neutral Lewis base L, such as, for example, an alkene or an alkyne. Complexes of this type and the use thereof as precursors in the CVD (chemical vapour deposition) process are described, for example, in U.S. Pat. No. 5,220,044, WO 00/71550, WO 00/17278, U.S. Pat. No. 6,130,345 or in Chem. Mater. 2001, 13, 3993; Inorg. Chem. 2001, 40, 6167; Chem. Mater. 1992, 4, 365; Organometallics 2001, 20, 4001. Preference is given to the use of fluorine-containing β-diketonate ligands, such as, for example, hexafluoroacetyl acetonate, since the corresponding copper(I) complexes have much higher thermal stability and higher volatility than their fluorine-free analogues. Fluorine-free copper(I) β-diketonate complexes, such as, for example, alkyne-stabilized copper(I) acetylacetonates, are extremely sensitive to oxygen, decompose even at 0° C. (Chem. Ber. 1995, 128, 525) and are thus not suitable as precursors for the CVD process. The copper layer is deposited in a thermally induced disproportionation reaction in accordance with the following equation:

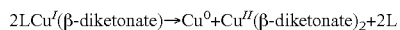

2LCu$^I$(β-diketonate)→Cu$^0$+Cu$^{II}$(β-diketonate)$_2$+2L

The resultant Cu$^{II}$(β-diketonate)$_2$ and the Lewis base L are volatile under the conditions used in the CVD process and can thus be removed from the system. Ideally, a high-purity copper film remains. However, only 50% of the copper(I) precursor employed can be converted into copper(0) in this reaction; the remaining 50% end up in the corresponding Cu$^{II}$(β-diketonate)$_2$. The same result is obtained on use of β-keto esters instead of β-diketones, as described, for example, in WO 00/08225 or in U.S. Pat. No. 5,441,766. However, it has proven disadvantageous on use of fluorine-containing copper (I) precursors that the adhesion of the copper films to various substrate surfaces is not optimal, which can probably be attributed to the van der Waals forces of the fluorine atoms in the precursor molecule and thus to repulsive interactions. In addition, there is a risk of contamination of the wafer in microelectronics, especially of the silicon with fluorine, which results in the wafer being unusable.

Complete conversion of the copper is achieved with Lewis base-stabilised copper(I) alkoxides of the formula LCu$^I$OR (EP 0468396) and with Lewis base-stabilised cyclopentadienylcopper(I) compounds of the formula LCu$^I$(η$^5$-C$_5$R$_5$), described in EP 0297348 and DE 4124686. Some of the examples in the cited patents are even fluorine-free and stable at 25° C. However, since the thermal decomposition reactions do not proceed in a defined way in these cases, free-radical species are formed in the decomposition reactions, unfortunately resulting in contaminated copper films (oxygen about 5%, carbon about 1%) (MRS Bulletin/August 1994, 41; Chem. Mater. 1992, 4, 577).

The object of the present invention was therefore to provide fluorine-free copper(I) precursors for the deposition of metallic copper which are simple and inexpensive to prepare, are thermally and if possible air stable, and can be converted fully into metallic copper films in a defined thermal decomposition reaction in the temperature range of about 50-400° C. with formation of defined molecular, copper-free, non-toxic and if possible gaseous by-products. Further objects of the present invention consist in providing a process for the preparation of the precursor substances according to the invention which is simple and inexpensive to carry out and a suitable process for the production of thin high-purity copper films or layers with the aid of these precursors and thus improved high-purity thin copper layers.

In accordance with the invention, the compounds of the general formula (II) are used for the production of high-purity thin copper-metal layers

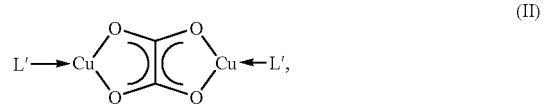

(II)

in which copper is in oxidation state +1, and

L' is an unsaturated hydrocarbon containing at least one olefinic or acetylenic group or CO, P(aryl)$_3$ or isonitrile RN≡C, where R is A, aryl or alkylaryl and A is straight-chain or branched C1-C30-alkyl, C3-C30-cycloalkyl, straight-chain or branched C2-C30-alkenyl, or straight-chain or branched C3-C30-cycloalkenyl, aryl is C6-C10-aryl, alkylaryl is C7-C18-alkylaryl.

Good results are obtained using the compounds of the general formula (II) in which L' is an unsaturated hydrocarbon from the series consisting of open-chain C2-C30-alkenes and cyclic C4C30-alkenes, open-chain C2-C30-alkynes and cyclic C10-C30-alkynes, CO, P(aryl)3 and RN≡C, where R is A, aryl is phenyl and A is straight-chain or branched C1-C30-alkyl or C3-C30-cycloalkyl.

Particularly good results are achieved using the compounds of the general formula (II) in which L' is an unsaturated hydrocarbon from the series consisting of open-chain C2-C15-alkenes and cyclic C4C15-alkenes, open-chain C2-C15-alkynes and cyclic C10-C15-alkynes, CO, P(C$_6$H$_5$)$_3$ and RN≡C, where R is A and A is straight-chain or branched C1-C8-alkyl or C3-C10-cycloalkyl.

From this group, very particular preference is given to compounds in which open-chain C2-C15-alkene is ethene, propene, the isomers of butene, pentene, hexene, heptene, octene, nonene or decene, and/or cyclic C4-C15-alkene is cyclobutene, cyclopentene, cyclohexene, cycloheptene, cyclooctene, cyclopentadiene, cyclohexadiene, cyclooctadiene, norbornene or norbornadiene, which may be substituted by a hydrocarbon, and/or open-chain C2-C15-alkyne is acetylene, propyne, the isomers of butyne, pentyne, hexyne, heptyne, octyne, nonyne, decyne or diphenylacetylene, and/or cyclic C10-C15-alkyne is cyclodecyne, cyclodecadiyne, cyclododecyne or cyclododecadiyne, which may be substituted-by a-hydrocarbon. Equally-preferred are compounds in which L' is one of the isonitriles cyclohexyl isonitrile or phenyl isonitrile.

The object according to the invention is preferably achieved by compounds of the general formula (I)

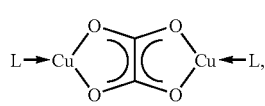

(I)

in which copper is in oxidation state +1, and

L is a hydrocarbon from the series consisting of open-chain alkyne of the formula R—C≡C—R' and cyclic C10-C20-alkyne and open-chain internal alkene of the formula R"HC═CHR'" and cyclic C4-C20-alkene, where R and R' are H, A, alkylaryl or alkynyl, R" and R'" are A, aryl, alkylaryl or alkynyl, where L, R, R', R" and R'" may each, independently of one another, adopt identical or different meanings in different positions of the molecule, and A is straight-chain or branched C1-C30-alkyl, C3-C30-cycloalkyl, straight-chain or branched C2-C30-alkenyl, or straight-chain or branched C3-C30-cycloalkenyl, aryl is C6-C10-aryl, alkylaryl is C7-C18-alkylaryl, alkynyl is straight-chain or branched C2-C30-alkynyl.

These novel compounds are a further subject-matter of the present invention.

Compounds according to the invention are preferably also compounds of the general formula (I) in which A is straight-chain or branched C1-C9-alkyl, straight-chain or branched C3-C9-cycloalkyl, straight-chain or branched C2-C9-alkenyl, or straight-chain or branched C3-C9-cyclo-alkenyl, aryl is phenyl or naphthyl, alkylaryl is tolyl or mesityl, alkynyl is straight-chain or branched C2-C9-alkynyl, and L, R, R', R" and R'" may each, independently of one another, adopt identical or different meanings in different positions of the molecule.

Further preferred sub-groups are formed by compounds of the general formula (I) in which

I.

A is straight-chain or branched C1-C4alkyl from the group consisting of methyl, ethyl, n- and i-propyl and n-, i- and tert-butyl, C3-C6-cycloalkyl from the group consisting of cyclopropyl, cyclobutyl, cyclopentyl and cyclohexyl, straight-chain or branched C2-C6-alkenyl from the group consisting of vinyl, propenyl, butenyl, pentenyl and hexenyl, or C3-C6-cycloalkenyl from the group consisting of cyclopropenyl, cyclobutenyl, cyclopentenyl, cyclopentadienyl and methyl-cyclopentadienyl, aryl is phenyl or naphthyl, alkylaryl is tolyl or mesityl, alkynyl is straight-chain or branched C2-C6-alkynyl from the group consisting of ethynyl, propynyl, butynyl, pentynyl and hexynyl, and R, R', R" and R'" may each, independently of one another, adopt identical or different meanings in different positions of the molecule, or

II.

in which L is an open-chain alkyne selected from the group consisting of Me-C≡C—Me, Et-C≡C—Et, Pr—C≡C—Pr and Bu-C≡C—Bu or

III.

in which L is a cyclic alkyne selected from the group consisting of cyclodecyne, cyclodecadiyne, cyclododecyne and cyclododecadiyne or

IV.

in which L is an open-chain internal alkene selected from the group consisting of HR"C═CHR'", in which R" and R'" are, independently of one another, $CH_3$, $C_2H_5$, $C_3H_7$ or $C_4H_9$, or

V.

in which L is a cyclic alkene selected from the group consisting of cyclobutene, cyclopentene, cyclopentadiene, cyclohexene, cyclohexadiene, cycloheptene, cycloheptadiene, cyclooctene, cyclooctadiene, norbornene and norbornadiene.

The object of the present invention is particularly preferably achieved by the novel compounds of the general formula (I)

di[(3-hexyne)copper(I)]oxalate and di[(norbornene)copper(I)]oxalate.

The compounds according to the invention or compounds which can be used in accordance with the invention can be obtained by a process in which $Cu_2O$ is reacted with oxalic acid and a Lewis base L in an inert solvent, and the resultant product is isolated. This process is likewise a subject-matter of the present invention.

High-purity thin copper-metal layers are produced by a process in which compounds of the general formula (II) are heated, causing the elimination of the Lewis base L' and deposition of metallic copper by decarboxylation. This production process is also a subject-matter of the present invention.

The elimination of the Lewis base L' is preferably carried out in a temperature range of from about 50 to about 200° C. The decarboxylation with formation of metallic copper and carbon dioxide which takes place as the second reaction is preferably completed in a temperature range of from about 150 to 350° C.

The eliminated Lewis base L' is preferably recycled, re-employed in a process for the preparation of the compounds of the general formula (II) and used for the production of high-purity thin metallic copper layers.

The object according to the invention is thus achieved, in particular, by high-purity thin metallic copper layers having improved properties produced using a compound of the general formula (II) in the process according to the invention.

DETAILED DESCRIPTION OF THE INVENTION

Figure 1:
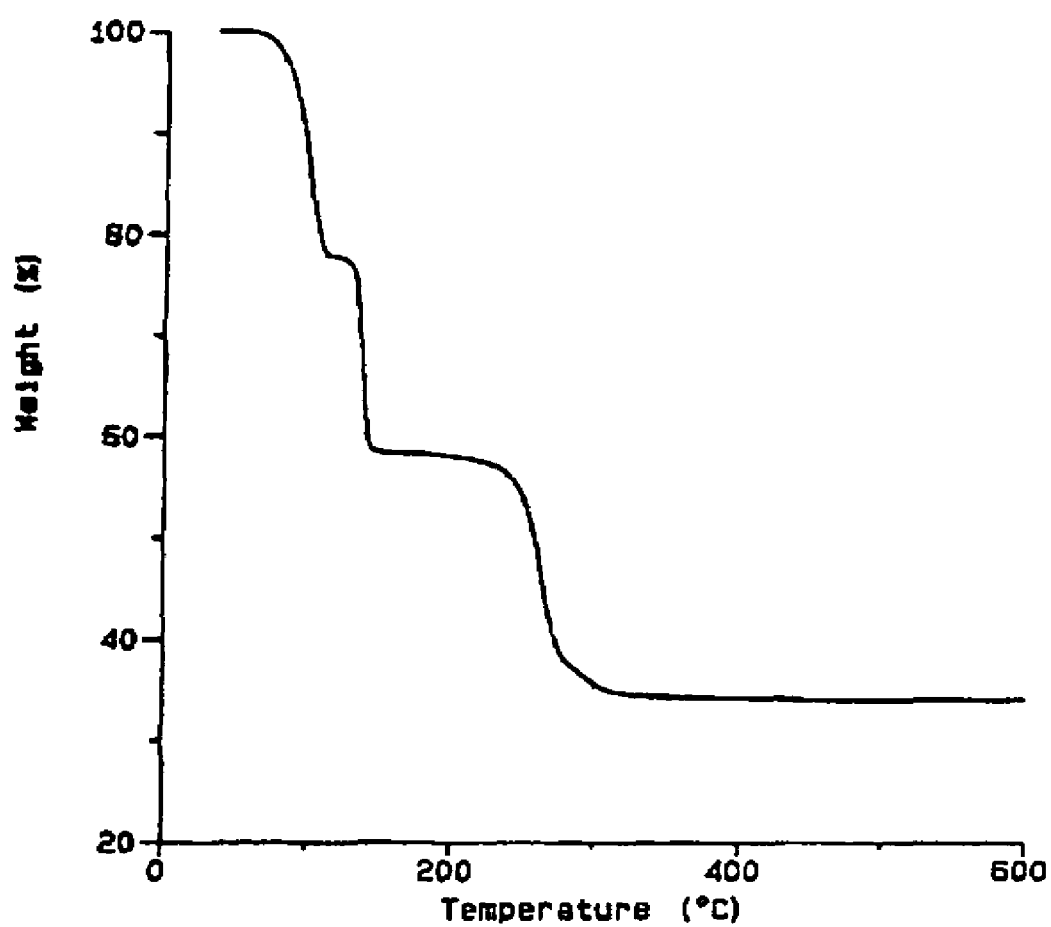
FIG. 1 shows the decomposition of the di[(3-hexyne)copper(I)] oxalate prepared as described in Example 1 as a function of the temperature with deposition of a thin copper layer on a substrate (TGA measurement).

The present invention provides compounds of the general formula (I)

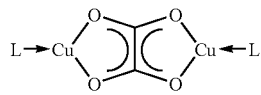  (I)

in which, in each case independently of the position in the complex and independently of one another, L is an open-chain alkyne R—C≡C—R' or a cyclic alkyne, or an open-chain alkene R"HC=CHR'" or a cyclic alkene. The oxidation state of the copper is +1.

R and R' may, independently of one another, be H or a hydrocarbon from the series consisting of alkyl, cycloalkyl, alkenyl, cycloalkenyl, alkylaryl and alkynyl.

R" and R'" may, independently of one another, be a hydrocarbon from the series consisting of alkyl, cycloalkyl, alkenyl, cycloalkenyl, aryl, alkylaryl and alkynyl.

The compound of the general formula (I) is prepared by reaction of $Cu_2O$, oxalic acid and the neutral ligand L or the two different neutral ligands in an inert aprotic organic solvent. The compounds of the general formula (I) can be isolated in pure form as temperature-stable substances. In addition, the substances obtained are distinguished by surprisingly and unusually high oxidation stability and can be handled in air without problems, which enormously simplifies subsequent use of the substances as precursors for the deposition of metallic copper.

Heating of the compounds of the general formula (II)

  (II)

in which copper is in oxidation state +1, and
   L' is an unsaturated hydrocarbon containing at least one olefinic or acetylenic group or CO, P(aryl)$_3$ or isonitrile RN≡C,
where
   R is alkyl, cycloalkyl, alkenyl, cycloalkenyl, aryl, alkylaryl or alkynyl, leaves a high-purity copper mirror; all by-products are volatile and can thus be removed very simply from the reaction site. The thermal decomposition proceeds in accordance with the following equation:

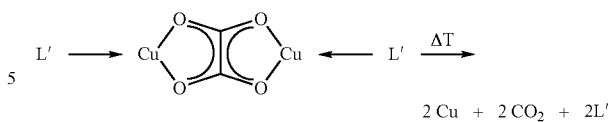

Besides metallic copper, the only reaction products formed are carbon dioxide and the Lewis base L', which can be regenerated and re-used.

The compounds of the general formula (II) can be used as precursors for the deposition of metallic copper. The deposition can be carried out from the gas phase or from a solution of the precursor and a suitable solvent or from the solid state of the precursor by contact of the precursor with a heated substrate. Compared with the prior art, it is advantageous firstly that copper(I) precursors are accessible with which metallic copper can be deposited, preferably quantitatively, in a defined decomposition reaction with no free radicals with formation of high-purity copper films. The yield of deposited metallic copper can thus be increased from 50 to 100% compared with the prior art. The high stability and insensitivity of the compounds, in particular the high oxidation stability, enormously simplify handling of the compounds in the process for the deposition of metallic copper and thus reduce the costs of the deposition process.

The advantages of the compounds of the general formula (II) compared with the substance used in accordance with the prior art (CupraSelect®) are thus: better physical properties, such as higher thermal stability, better chemical properties, such as higher oxidation stability, simpler handling, less expensive synthesis owing to the much less expensive starting material oxalic acid compared with hexafluoroacetylacetone, twice the yield of metallic copper in the deposition process, copper-free and non-toxic by-products, fewer by-products and thus lower environmental pollution. In addition, the compounds contain no fluorine atoms which can result in fluorine contamination and thus in wafers being unusable.

Overall, the synthesis of the copper(I) precursors according to the invention is thus simpler and less expensive than that of the commercially available copper(I) precursor CupraSelect®, which is (trimethylvinylsilane)copper(I) hexafluoroacetylacetonate. At the same time, the precursors according to the invention enable both the quality of the copper coatings to be increased and the process to be carried out in a more environmentally friendly manner.

Compounds of the general formula (I) according to the invention contain an oxalate dianion, two copper centres in oxidation state +1 and at least two neutral ligands L, where the oxalate dianion is bonded to the two copper(I) centres as a bridge in µ-1,2,3,4 mode. The dicopper(I) oxalate unit $CuO_2C_2O_2Cu$ is stabilised by coordination of at least two neutral ligands L to the two copper(I) centres, preferably of two identical ligands L, so that the two copper(I) centres have at least a pseudotrigonal-planar, possibly also a tetrahedral environment. The copper atoms present in the complex can be bonded to two different ligands L. For simplification, the following text refers generally to the ligand or the Lewis base L although this may also be taken to mean two different ligands or Lewis bases L.

L is an open-chain alkyne R—C≡C—R' or cyclic C10-C20-alkyne or an open-chain alkene R"HC=CHR'" or cyclic C4-C20-alkene. R and R' may in turn, independently of one another, be H, alkyl, cycloalkyl, alkenyl, cycloalkenyl, alkylaryl or alkynyl. R" and R'" may, independently of one another, be alkyl, cycloalkyl, alkenyl, cycloalkenyl, aryl, alkylaryl or alkynyl.

Cyclic C10-C20-alkyne may be straight-chain or branched C10-C20-cycloalkyne, preferably straight-chain or branched C10-C15-cycloalkyne, particularly preferably C10-C12-cycloalkyne from the series consisting of cyclodecyne, cyclodecadiyne, cyclododecyne and cyclododecadiyne.

Cyclic C4-C20-alkene may be straight-chain or branched C4-C20-cycloalkene, preferably straight-chain or branched C4-C15-cycloalkene, particularly preferably C4-C8-cycloalkene from the series consisting of cyclobutene, cyclopentene, cyclopentadiene, cyclohexene, cyclohexadiene, cycloheptene, cycloheptadiene, cyclooctene, cyclooctadiene, norbornene and norbornadiene.

Alkyl groups may be straight-chain or branched C1-C30-alkyl, preferably straight-chain or branched C1-C9-alkyl, particularly preferably straight-chain or branched C1-C4-alkyl from the group consisting of methyl, ethyl, n- and i-propyl and n-, i- and tert-butyl. Cycloalkyl groups may be straight-chain or branched C3-C30-cycloalkyl, preferably C3-C9-cycloalkyl, particularly preferably C3-C6-cycloalkyl from the group consisting of cyclopropyl, cyclobutyl, cyclopentyl and cyclohexyl.

Alkenyl groups may be straight-chain or branched C2-C30-alkenyl, preferably straight-chain or branched C2-C9-alkenyl, particularly preferably straight-chain or branched C2-C6-alkenyl from the group consisting of vinyl, propenyl, butenyl, pentenyl and hexenyl. Cycloalkenyl groups may be straight-chain or branched C3-C30-cycloalkenyl, preferably C3-C9-cycloalkenyl, particularly preferably C3-C6-cycloalkenyl from the group consisting of cyclopropenyl, cyclobutenyl, cyclopentenyl, cyclopentadienyl and methylcyclopentadienyl.

Aryl groups may be C6-C10-aryl, preferably phenyl or naphthyl. Alkylaryl may be C7-C18-alkylaryl, preferably tolyl or mesityl.

Alkynyl groups may be straight-chain or branched C2-C30-alkynyl, preferably straight-chain or branched C2-C9-alkynyl, particularly preferably straight-chain or branched C2-C6-alkynyl from the group consisting of ethynyl, propynyl, butynyl, pentynyl and hexynyl.

Particularly suitable neutral Lewis bases are open-chain alkynes of the formula R-C≡C—R', cyclic alkynes, open-chain alkenes of the formula R"HC=CHR'" and cyclic alkenes. Preference is given to the use of open-chain alkynes from the group consisting of R-C≡C—R', and particularly good results are obtained with the alkynes R—C≡C—R' (R and R'=CH$_3$, C$_2$H$_5$, C$_3$H$_7$ or C$_4$H$_9$). Preference is given to the use of open-chain alkenes from the group consisting of R"HC=CHR'" (R" and R'"=CH$_3$, C$_2$H$_5$, C$_3$H$_7$ or C$_4$H$_9$) and cyclic alkenes, and particularly good properties are obtained with the cyclic alkenes cyclohexene and norbornene. Particularly good results are obtained with the alkyne Et-C≡C—Et and the alkene norbornene.

The compound of the general formula (I) is preferably prepared by reaction of Cu$_2$O, oxalic acid and the Lewis base L under a protective-gas atmosphere in an inert aprotic organic solvent. For this purpose, two different Lewis bases L in an equimolar ratio can be employed as Lewis base L. The sequence of addition of the components can be selected as desired. If the Lewis base L employed is to be a mixture of two corresponding compounds, the two compounds are preferably added simultaneously to the reaction mixture or mixed with one another before the addition. The starting compounds can be pre-dissolved or suspended in a suitable solvent or added as a solid or liquid without a solvent. Suitable solvents for carrying out the reaction are inert aprotic solvents, such as open-chain or cyclic aliphatic and aromatic hydrocarbons, which may be partially halogenated, or ethers and cyclic ethers. Particular preference is given to the use of pentane, hexane, heptane, cyclohexane, toluene, methylene chloride, trichloromethane, chlorobenzene, diethyl ether or tetrahydrofuran. The protective-gas atmosphere used can be nitrogen or argon. The stoichiometric ratio of the starting materials Cu$_2$O, oxalic acid and the Lewis base L is between 1:1:2 and 1:1:4, preferably between 1:1:2 and 1:1:3 and is particularly preferably 1:1:2. The Lewis base L should not be added in less than the stoichiometric amount with respect to oxalic acid and Cu$_2$O. The reaction can be carried out in a temperature range of from −30 to +100° C., preferably from 0 to 50° C. and very preferably between 20 and 40° C. The highest yields are obtained at room temperature. The reaction time is between 1 and 24 hours, preferably between 2 and 8 hours and very preferably between 3 and 6 hours. The reaction solution changes from a red suspension to a colourless or brownish solution or suspension, depending on the nature of the complex formed. The insoluble constituents are separated off. This can be carried out by filtration, centrifugation or other methods known to the person skilled in the art. A clear colourless, yellow or red solution is obtained, depending on the type of Lewis base L employed. The compounds of the general formula (I) are subsequently isolated. This can be carried out by methods known to the person skilled in the art after removal of the solvent. Further purification is carried out if necessary. Instead of mechanical removal of the solids from the reaction mixture by filtration or other methods, an extraction can also be carried out for removal of the product formed. The compounds of the general formula (I) are, as already described above, surprisingly temperature-stable and can therefore be isolated well as pure substances and subsequently characterised analytically and spectroscopically.

Compounds of the general formula (II) according to the invention

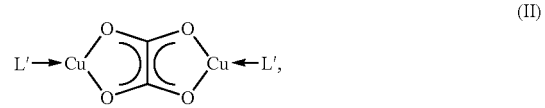

(II)

can be used for the production of high-purity thin copper-metal layers.

L' is an open-chain alkyne R-C≡C—R', cyclic alkyne, open-chain alkene RHC=CHR', cyclic alkene, CO, P(aryl)$_3$ or isonitrile RN≡C. R and R' may in turn, independently of one another, be H, alkyl, cycloalkyl, alkenyl, cycloalkenyl, aryl, alkylaryl or alkynyl.

The meanings of alkyl, cycloalkyl, alkenyl, cycloalkenyl, aryl, alkylaryl or alkynyl correspond to the meanings in the compounds of the general formula (I).

Cycloalkyne may be straight-chain or branched C10-C20-cycloalkyne, preferably straight-chain or branched C10-C15-cycloalkyne, particularly preferably C10-C12-cycloalkyne from the series consisting of cyclodecyne, cyclodecadiyne, cycloundecyne, cycloundecadiyne, cyclododecyne and cyclododecadiyne.

Cycloalkene may be straight-chain or branched C4C20-cycloalkene, preferably straight-chain or branched C4-C15-cycloalkene, particularly preferably C4-C8-cycloalkene from the series consisting of cyclobutene, cyclopentene, -cyclopentadiene, cyclohexene, cyclohexadiene, cycloheptene, cycloheptadiene, cyclooctene, cyclooctadiene, norbornene and norbornadiene.

Particularly suitable neutral Lewis bases L' are open-chain alkynes of the formula R-C≡C—R', cyclic alkynes, open-chain alkenes of the formula RHC=CHR', cyclic alkenes, CO, P(aryl)$_3$ and RN≡C. Preference is given to the use of open-chain alkynes from the group consisting of R-C≡C—R', open-chain alkenes of the formula RHC=CHR', cyclic alkenes, CO and RN≡C. Particularly good results are obtained with the alkynes R—C≡C—R' (R and R'=CH$_3$, C$_2$H$_5$, C$_3$H$_7$ or C$_4$H$_9$), with the open-chain alkenes RHC=CHR' (R and R'=CH$_3$, C$_2$H$_5$, C$_3$H$_7$ or C$_4$H$_9$), with the cyclic alkenes cyclohexene and norbornene, with CO and RN≡C (R='C$_4$H$_9$, C$_6$H$_{11}$ or C$_6$H$_5$). Preference is given to the use of open-chain alkenes from the group consisting of RHC=CHR' (R and R'=CH$_3$, C$_2$H$_5$, C$_3$H$_7$ or C$_4$H$_9$), the cyclic alkenes cyclohexene and norbornene, CO and C$_6$H$_{11}$N≡C, and particularly good properties are obtained with the open-chain alkyne Et-C≡C—Et, the cyclic alkene norbornene, CO and C$_6$H$_{11}$N≡C. Particularly good results are obtained with the alkyne Et-C≡C—Et and the alkene norbornene.

The thermal behaviour of the compounds can be investigated by TGA (thermogravimetric analysis) and DSC (differential scanning calorimetry). Investigations carried out have shown that the decomposition of the compounds according to the invention takes place in two main steps:

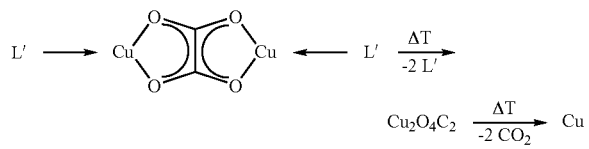

Firstly, the Lewis base L' is eliminated from the copper(I) complex. This elimination can also take place in steps, depending on the compound, and can be detected by TGA. In the second step, decarboxylation takes place through an internal redox reaction of the remaining fragment CuO$_2$C$_2$O$_2$Cu, with formation of metallic copper and carbon dioxide. The first step takes place, depending on the precursor, in a temperature range of from about 50 to about 200° C., and the second from about 150° C. and is complete at about 350° C. However, it is perfectly possible for the elimination of the Lewis bases and the decarboxylation reaction to proceed in parallel at the transition to higher temperatures. The residual content corresponds precisely to the copper content in the corresponding copper(I) precursor, so that the yield of metallic copper is 100% with the compounds of the general formula (II) and is thus twice as high as that in the prior art.

This efficient decomposition reaction causes the formation of fewer by-products with the compounds of the general formula (II) compared with the prior art. The free Lewis base L' re-forms in the deposition process and can be collected by appropriate equipment, such as, for example, cold traps in the exhaust air, and re-used; the second by-product formed is carbon dioxide. The by-products are thus copper-free, non-toxic and thus less hazardous compared with the prior art, in which copper(II) hexafluoroacetylacetonate and the Lewis base trimethylvinylsilane are formed as by-products. The environmental pollution is thus considerably lower than on use of the compounds from the prior art.

(Norbornene)$_2$Cu$_2$O$_4$C$_2$ has proven to be a thermally stable and very oxidation-insensitive compound. The compound is stable up to 100° C. and can be handled in air over an extended period. This is an enormous advance compared with the prior art, since CupraSelect® decomposes slowly even from about 50° C., and the compound is also oxidised rapidly in air to give copper(II). This enables very much simpler handling, not only in the synthesis, but also in the deposition process.

The compounds of the general formula (II) can be used as precursors for the deposition of metallic copper. The deposition of metallic copper films can be carried out from the gas phase or from a solution of the precursor and a suitable solvent or from the solid state of the precursor by contact of the precursor with a heated substrate.

Examples are given below for illustration and for better understanding of the present invention. However, these are not suitable, owing to the general validity of the inventive principle described, for reducing the scope of protection of the present application merely to these examples. Furthermore, the contents of the cited patent applications are to be regarded as part of the disclosure content of the present invention, which is based on the description.

EXAMPLES

Example 1

Di[(3-hexyne)copper(I)]oxalate 3 ml of EtC≡CEt and 1.1 g of oxalic acid are added to a suspension of 1.8 g of Cu$_2$O in 30 ml of methylene chloride under an inert-gas atmosphere, and the mixture is stirred at room temperature for 4 hours. In order to remove insoluble residues, the solution is passed through a frit with silica gel, and the residue is washed twice on the frit with methylene chloride. The colourless solution is evaporated, and colourless crystals of (EtC≡CEt)$_2$Cu$_2$O$_4$C$_2$ are obtained at −30° C.

C$_{14}$H$_{20}$Cu$_2$O$_4$ (379.40 g/mol). Analysis [%]: calculated: C 44.3, H 5.3, found: C 44.7, H 4.9. IR (KBr) [cm$^{-1}$]: $\nu_{C≡C}$ 2053, 2020 (w), $\nu_{CO2}$ 1645 (vs), 1355 (w), 1314 (m). $^1$H-NMR (CDCl$_3$): δ 1.22 (t, 12 H, $^3$J=7.3 Hz, CH$_3$), 2.49 (q, 8 H, $^3$J=7.4 Hz, CH$_2$). $^{13}$C{$^1$H}NMR (CDCl$_3$): δ 14.4 (CH$_3$), 15.5 (CH$_2$), 87.6 (C≡C), 171.4 (COO). MS (m/e (%)): 525 (7) [M+Cu(EtC≡CEt)]$^+$, 443 (7) [M+Cu]$^+$, 227 (100) [M−CuO$_4$C$_2$]$^+$, 145 (96) [M−(EtC≡CEt)CuO$_4$C$_2$]$^+$, TG (30-1000° C., 5° C./min) three-stage decomposition, 1st stage temperature range 60-120° C. weight reduction 22% (EtC≡CEt), 2nd stage temperature range 120-150° C. weight reduction 19% (EtC≡CEt), 3rd stage temperature range 200-310° C., weight reduction 24% (2 CO$_2$), residual content 35% (2 Cu).

FIG. 1 shows the decomposition of the prepared di[(3-hexyne)copper(I)]oxalate as a function of the temperature with deposition of a thin copper layer on a substrate.

Example 2

Di[(norbornene)copper(I)]oxalate 2.4 g of norbornene and 1.1 g of oxalic acid are added to a suspension of 1.8 g of Cu$_2$O in 50 ml of methylene chloride under an inert-gas atmosphere, and the mixture is stirred at room temperature for 5 hours. In order to remove insoluble residues, the solution is passed through a frit with silica gel, and the residue is washed twice on the frit with methylene chloride. The colourless solution is evaporated, and colourless crystals of (norbornene)$_2$Cu$_2$O$_4$C$_2$ are obtained at −30° C.

$C_{16}H_{20}Cu_2O_4$ (403.43 g/mol). IR (KBr) [cm$^{-1}$]: $v_{C=C}$ 1473 (w); $v_{CO2}$ 1644 (m), 1362 (m), 1303 (vs). $^1$H-NMR (CDCl$_3$) [ppm]: 1.00 (d, $^2$J=7.8 Hz, 2 H, H$_{endo}$), 1.03 (d, $^2$J=9.5 Hz, 1 H, H$_{anti}$), 1.28 (d, $^2$J=9.6 Hz, 1 H, H$_{syn}$), 1.59 (d, $^2$J=7.7 Hz, 2 H, H$_{exo}$), 3.08 (s, 2 H, CH), 5.25 (s, 2 H, =CH). $^{13}$C{$^1$H}NMR (CDCl$_3$) [ppm]: 24.4 (CH$_2$CH$_2$), 42.7 (CHCH$_2$), 45.7 (CHCH$_2$CH), 109.2 (=CH), 171.4 (COO). TG (30-1000° C., 5° C./min) two-stage decomposition, 1st stage temperature range 100-150° C. weight reduction 46% (2 norbornene), 2nd stage temperature range 200-300° C., weight reduction 23% (2 CO$_2$), residual content 31% (2 Cu).

Figure 2:
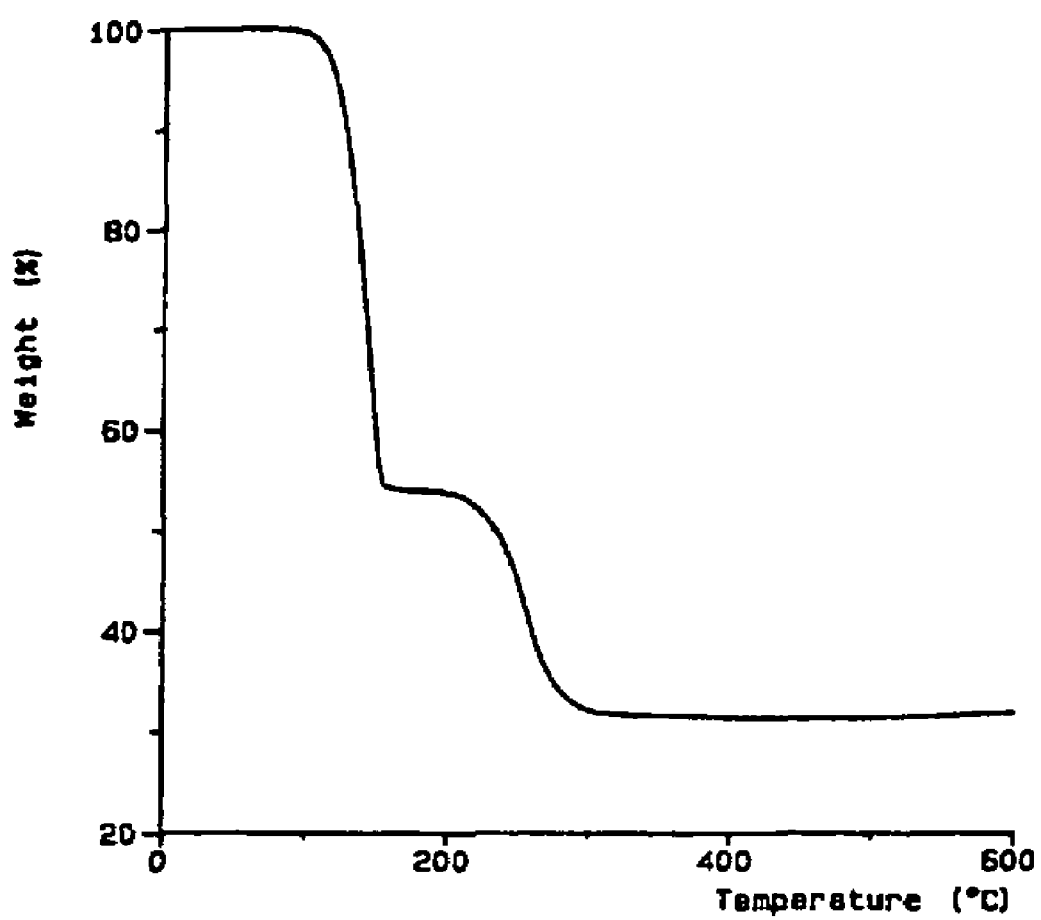
FIG. 2 shows the decomposition of the di[(norbornene) copper(I)] oxalate prepared as described in Example 2 as a function of the temperature with deposition of a thin copper layer on a substrate (TGA measurement).

FIG. 2 shows the decomposition of the prepared di[(norbornene)copper(I)]oxalate as a function of the temperature with deposition of a thin copper layer on a substrate.

The invention claimed is:

1. A compound of the general formula (II)

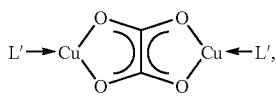

(II)

wherein copper is in oxidation state +1, wherein
L' is an unsaturated hydrocarbon comprising at least one olefinic group, at least one acetylenic group, at least one CO, at least one P(aryl)$_3$ group, at least one isonitrile RN≡C, or a combination thereof,
wherein
R is A, aryl or alkylaryl, wherein
A is a straight-chain C1-C30-alkyl, a branched-chain C1-C30-alkyl, a C3-C30-cycloalkyl, a straight-chain C2-C30-alkenyl, a branched-chain C2-C30-alkenyl, an unbranched C3-C30-cycloalkenyl, or a branched C3-C30-cycloalkenyl, wherein
aryl is C6-C10-aryl, and
alkylaryl is C7-C18-alkylaryl.

2. The compound of claim 1 wherein
L' is an unsaturated hydrocarbon selected from the group consisting of open-chain C2-C30-alkenes, cyclic C4-C30-alkenes, open-chain C2-C30-alkynes, cyclic C10-C30-alkynes, CO, P(aryl)$_3$ and RN≡C,
wherein
R is A, wherein
aryl is phenyl
and wherein
A is a straight-chain C1-C30-alkyl, a branched-chain C1-C30-alkyl, or a C3-C30-cycloalkyl.

3. The compound of claim 1, wherein
L' is an unsaturated hydrocarbon selected from the group consisting of an open-chain C2-C15-alkene, a cyclic C4-C15 alkene, an open-chain C2-C15-alkyne, a cyclic C10-C15-alkyne, CO, P(C$_6$H$_5$)$_3$ and RN≡C,
wherein
R is A, and wherein
A is a straight-chain C1-C8-alkyl, a branched-chain C1-C8-alkyl, or a C3-C10-cycloalkyl.

4. The compound of claim 3 wherein the open-chain C2-C15-alkene is selected from the group consisting of ethene, propene, the isomers of butene, pentene, hexene, heptene, octene, nonene and decene, wherein the cyclic C4-C15-alkene is selected from the group consisting of cyclobutene, cyclopentene, cyclohexene, cycloheptene, cyclooctene, cyclopentadiene, cyclohexadiene, cyclooctadiene, norbornene and norbornadiene, which may be substituted by a hydrocarbon, wherein the open-chain C2-C15-alkyne is selected from the group consisting of acetylene, propyne, the isomers of butyne, pentyne, hexyne, heptyne, octyne, nonyne, decyne and diphenylacetylene, wherein the cyclic C10-C15-alkyne is selected from the group consisting of cyclodecyne, cyclodecadiyne, cyclododecyne and cyclododecadiyne, which may be substituted by a hydrocarbon, and wherein L' is selected from the group consisting of isonitriles, cyclohexyl isonitrile and phenyl isonitrile.

5. A compound of the general formula (I)

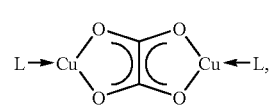

(I)

wherein copper is in oxidation state +1, wherein
L is a hydrocarbon selected from the group consisting of an open-chain alkyne of the formula R—C≡C—R', a cyclic C10-C20-alkyne, an open-chain internal alkene of the formula R" HC=CHR''' and a cyclic C4-C20-alkene,
wherein
R and R' are H, A, alkylaryl or alkynyl, wherein
R" and R''' are A, aryl, alkylaryl or alkynyl, wherein
L, R, R', R" and R''' may each, independently of one another, adopt identical or different meanings in different positions of the molecule,
wherein
A is straight-chain C1-C30 alkyl, a branched-chain C1-C30-alkyl, a C3-C30-cycloalkyl, a straight-chain C2-C30 alkenyl, a branched-chain C2-C30-alkenyl, a straight-chain C3-C30 cycloalkenyl, or a branched C3-C30-cycloalkenyl, wherein
aryl is C6-C10-aryl, wherein
alkylaryl is C7-C18-alkylaryl, and wherein
alkynyl is a straight-chain or a branched-chain C2-C30-alkynyl.

6. A process for the production of a high-purity thin copper-metal layer, comprising
heating the compound of claim 1 to form metallic copper, and
depositing the metallic copper to form the high-purity copper-metal layer.

7. The process of claim 6, wherein the heating comprises
a) heating at a temperature range of from 50 to about 200° C., thereby forming a fragment through elimination of the Lewis base L from the compound of general formula (II); and
b) heating the fragment to a temperature range of from 150 to 300° C., thereby forming the metallic copper through decarboxylation of the fragment.

8. The process of claim 7, wherein the eliminated Lewis base L is recycled.

9. The compound of claim 5, wherein
A is a straight-chain or a branched-chain C1-C9-alkyl, a straight-chain or a branched-chain C3-C9-cycloalkyl, a straight-chain or a branched-chain C2-C9-alkenyl, or a straight-chain or a branched-chain-C3-C9-cycloalkenyl, wherein
aryl is phenyl or naphthyl, wherein
alkylaryl is tolyl or mesityl, wherein
alkynyl is a straight-chain or a branched-chain C2-C9-alkynyl, and wherein L, R, R', R" and R'" may each, independently of one another, adopt identical or different meanings in different positions of the molecule.

10. The compound of claim 5, wherein
A is a straight-chain or a branched-chain C1-C4-alkyl selected from the group consisting of methyl, ethyl, n-propyl, i-propyl, n-butyl, i-butyl, and tert-butyl; a C3-C6-cycloalkyl selected from the group consisting of cyclopropyl, cyclobutyl, cyclopentyl and cyclohexyl; a straight-chain or a branched-chain C2-C6-alkenyl selected from the group consisting of vinyl, propenyl, butenyl, pentenyl and hexenyl; or a C3-C6-cycloalkenyl selected from the group consisting of cyclopropenyl, cyclobutenyl, cyclopentenyl, cyclopentadienyl and methyl-cyclo-pentadienyl, wherein aryl is phenyl or naphthyl, wherein alkylaryl is tolyl or mesityl, wherein alkynyl is straight-chain or a branched-chain C2-C6-alkynyl selected from the group consisting of ethynyl, propynyl, butynyl, pentynyl and hexynyl, and wherein R, R', R" and R'" may each, independently of one another, adopt identical or different meanings in different positions of the molecule.

11. The compound of claim 5, wherein L is an open-chain alkyne selected from the group consisting of Me-C≡C—Me, Et-C≡C-Et, Pr—C≡C—Pr and Bu-C≡C-Bu.

12. The compound of claim 5, wherein L is a cyclic alkyne selected from the group consisting of cyclodecyne, cyclodecadiyne, cyclododecyne and cyclo-dodeca-diyne.

13. The compound of claim 5, wherein L is HR"C=CHR'", wherein R" and R'" are, independently of one another, $CH_3$, $C_2H_5$, $C_3H_7$ or $C_4H_9$.

14. The compound of claim 5, wherein L is a cyclic alkene selected from the group consisting of cyclobutene, cyclopentene, cyclopentadiene, cyclohexene, cyclohexadiene, cycloheptene, cycloheptadiene, cyclooctene, cyclooctadiene, norbornene and norbornadiene.

15. The compound of claim 5, wherein the compound is di[(3-hexyne)copper(I)] oxalate or di[(norbornene)copper (I)] oxalate.

16. A process for preparing the compound of claim 5, comprising reacting $Cu_2O$ with oxalic acid and at least one Lewis base L in an inert solvent to form the compound of claim 5, and isolating the compound of claim 5.

17. The process of claim 16, further comprising an inert aprotic organic solvent wherein the inert aprotic organic solvent is an open-chain apliphatic hydrocarbon, a cyclic aliphatic hydrocarbon, an aromatic hydrocarbon, a halogenated aliphatic hydrocarbon, a halogenated aromatic hydrocarbon; a linear ether, a cyclic ether, or a mixture thereof.

18. The process of claim 16, wherein the process is carried out under a protective-gas atmosphere.

19. The process of claim 16, wherein the at least one Lewis base L is employed in excess of at least twice the stoichiometric ratio of the starting materials $Cu_2O$ and oxalic acid.

20. The process of claim 16, wherein the starting materials $Cu_2O$, oxalic acid and the at least one Lewis base L are employed in a stoichiometric ratio of from 1:1:2 to 1:1:4.

21. The process of claim 16, wherein the at least one Lewis base L comprises two different Lewis bases L which are employed in the same molar amounts.

22. The process of claim 16, wherein the reaction is carried out within a reaction time of from 1 to 24 hours a and at a temperature range of from −30 to +100° C.

23. The process of claim 16, wherein the isolating further comprises separating off insoluble constituents.

* * * * *